(12) United States Patent
Le et al.

(10) Patent No.: US 8,747,392 B2
(45) Date of Patent: Jun. 10, 2014

(54) HANDHELD MEDICAL DEVICE

(75) Inventors: Richard T. Le, Irvine, CA (US); Daniel M. Santos, Laguna Niguel, CA (US); Patrick L. Johnson, Cowan Heights, CA (US)

(73) Assignee: Pro-Dex, Inc., Irvine, CA (US)

( * ) Notice: Subject to any disclaimer, the term of this patent is extended or adjusted under 35 U.S.C. 154(b) by 1484 days.

(21) Appl. No.: 12/122,400

(22) Filed: May 16, 2008

(65) Prior Publication Data

US 2008/0287925 A1    Nov. 20, 2008

Related U.S. Application Data

(60) Provisional application No. 60/938,654, filed on May 17, 2007.

(51) Int. Cl.
*A61B 17/00* (2006.01)

(52) U.S. Cl.
USPC .............. 606/1; 606/159; 606/167; 604/19; 604/23

(58) Field of Classification Search
None
See application file for complete search history.

(56) References Cited

U.S. PATENT DOCUMENTS

| | | |
|---|---|---|
| 5,383,785 A | 1/1995 | Brugger |
| 5,431,675 A | 7/1995 | Nicholas et al. |
| 5,520,634 A | 5/1996 | Fox et al. |
| 5,658,304 A | 8/1997 | Lim |
| 5,676,680 A | 10/1997 | Lim |
| 5,729,904 A | 3/1998 | Trott |
| 5,839,196 A | 11/1998 | Trott |
| 5,868,785 A | 2/1999 | Tal et al. |
| 5,871,493 A * | 2/1999 | Sjostrom et al. .............. 606/180 |
| 6,162,214 A | 12/2000 | Mueller et al. |
| 6,302,406 B1 | 10/2001 | Ventura |
| 6,312,441 B1 | 11/2001 | Deng |
| 6,432,119 B1 | 8/2002 | Saadat |
| 6,623,500 B1 | 9/2003 | Cook et al. |
| 6,656,133 B2 | 12/2003 | Voegele et al. |
| 6,780,189 B2 | 8/2004 | Tidwell et al. |
| 6,809,508 B2 | 10/2004 | Donofrio |
| 6,945,981 B2 | 9/2005 | Donofrio et al. |

(Continued)

FOREIGN PATENT DOCUMENTS

| | | |
|---|---|---|
| EP | 0 830 846 A | 3/1998 |
| EP | 830846 A1 * | 3/1998 |

(Continued)

OTHER PUBLICATIONS

International Search Report; Aug. 20, 2008, 4 pages.

(Continued)

*Primary Examiner* — Gary Jackson
*Assistant Examiner* — Joseph D Harris
(74) *Attorney, Agent, or Firm* — Knobbe, Martens, Olson & Bear, LLP

(57) ABSTRACT

A handheld medical device comprises an internal flow passage that is in axial alignment with an output drive shaft. The drive shaft is powered by a motor assembly that is offset from the internal flow passage and the output drive shaft. The drive shaft and the motor assembly can be connected by a gear train. A collet mechanism can be used to secure a surgical implement to the handheld medical device. A first button assembly and a second button assembly can be positioned on diametrically opposed portions of the handheld medical device.

19 Claims, 8 Drawing Sheets

(56) References Cited

U.S. PATENT DOCUMENTS

| | | |
|---|---|---|
| 6,958,071 B2 | 10/2005 | Carusillo et al. |
| 6,977,495 B2 | 12/2005 | Donofrio |
| 7,011,661 B2 | 3/2006 | Riedel et al. |
| 7,025,732 B2 | 4/2006 | Thompson et al. |
| 7,226,424 B2 | 6/2007 | Ritchart et al. |
| 7,237,990 B2 | 7/2007 | Deng |
| 7,990,005 B2 | 8/2011 | Walter et al. |
| 2001/0047183 A1 | 11/2001 | Privitera et al. |
| 2002/0040229 A1 | 4/2002 | Norman |
| 2003/0225411 A1 | 12/2003 | Miller |
| 2004/0158173 A1 | 8/2004 | Voegele et al. |
| 2004/0186479 A1 | 9/2004 | Tidwell et al. |
| 2004/0220602 A1 | 11/2004 | Deng et al. |
| 2005/0215921 A1 | 9/2005 | Hibner et al. |
| 2005/0277970 A1 | 12/2005 | Norman et al. |
| 2005/0283150 A1 | 12/2005 | Moutafis et al. |
| 2006/0052790 A1 | 3/2006 | Miller |
| 2006/0200040 A1 | 9/2006 | Weikel, Jr. et al. |
| 2006/0217729 A1 | 9/2006 | Eskridge et al. |
| 2006/0276797 A1 | 12/2006 | Botimer |
| 2007/0016211 A1 | 1/2007 | Botimer |
| 2007/0100362 A1 | 5/2007 | Deng |
| 2007/0156064 A1 | 7/2007 | Ritchart et al. |
| 2007/0179401 A1 | 8/2007 | Hibner |
| 2011/0213395 A1 | 9/2011 | Corrington et al. |

FOREIGN PATENT DOCUMENTS

| | | |
|---|---|---|
| EP | 0 905 432 A2 | 3/1999 |
| WO | WO 97/16124 A | 5/1997 |
| WO | WO 2008-144552 | 11/2008 |
| WO | WO 2011-1085392 | 7/2011 |

OTHER PUBLICATIONS

Written Opinion in PCT Application No. PCT/US2008/063962, mailed Aug. 20, 2008, 7 pages.

International Preliminary Report on Patentability in PCT Application No. PCT/US2008/063962, Jun. 30, 2009, 6 pages.

Office Action in corresponding European Application No. 08755751.8, dated Feb. 22, 2011, 3 pages.

Office Action in corresponding Chinese Application No. 200880016253.0, dated Jul. 25, 2011, 9 pages.

Office Action in corresponding Japanese application No. 2010-508613, mailed Dec. 6, 2011, 6 pages.

* cited by examiner

HANDHELD MEDICAL DEVICE

CROSS-REFERENCE TO RELATED APPLICATIONS

This application claims the priority benefit under 35 U.S.C. §119(e) of U.S. Provisional Patent Application No. 60/938,654, filed on May 17, 2007, which is incorporated by reference in its entirety.

BACKGROUND OF THE INVENTION

1. Field of the Invention

The present invention generally relates to handheld medical devices. More particularly, certain features, aspects and advantages of the present invention relate to such devices having control button assemblies on multiple sides, having an offset drive system, having a cannulated drive shaft and/or having a locking collet mechanism.

2. Description of the Related Art

Handheld medical devices are generally known in which a motor drives a surgical device having any of a number of different functions and operating characteristics. The surgical devices are interchangeable such that the same handpiece can be used with any of a number of surgical devices or cutter configurations.

In addition, U.S. Pat. No. 5,871,493 shows a handpiece in which fluid can be aspirated through the surgical device through an aspiration channel. The aspiration channel extends alongside a motor, which motor is axially aligned with the surgical device. Thus, the aspiration channel must be offset from the surgical device.

U.S. Pat. No. 6,221,088 shows a power handpiece for driving a surgical blade to cut anatomical tissue. A distal end of the handpiece couples to the surgical blade. A motor assembly can be installed in the handpiece to drive the surgical blade and a suction channel is provided in the handpiece body, with a portion of the handpiece body extending through a drive shaft that connects to the surgical blade. The surgical blade carries a sealing assembly to facilitate irrigation and suction. The motor is removed from the handpiece body for sterilization.

SUMMARY OF THE INVENTION

While these configurations may be adequate, each of these configurations also suffers from some drawbacks. Thus, an improved handheld medical device is desired. In some configurations, controls can be positioned on each of the proximal and distal ends of the handpiece. In some configurations, those controls can be positioned on each of an upper side and a lower side of the handpiece. In some configurations, a motor can be provided that has an axis offset from an axis of an implement that is driven by the motor. In some configurations, a fluid passage can be defined through the handpiece in which the axis of the implement extends along the fluid passage. In some embodiments, a collet mechanism features a locking member that is spring biased to a lock position and moveable with a button to an unlock position.

In some embodiments that are arranged and configured in accordance with certain features, aspects and advantages of the present invention, a medical handpiece comprises a handpiece outer housing. The handpiece outer housing encloses an elongated motor assembly. The elongated motor assembly comprises a motor output shaft. The motor output shaft rotates about a motor output shaft axis. The handpiece outer housing also encloses an internal fluid passage. The internal fluid passage extends generally parallel to the motor output shaft axis. The internal fluid passage also extends generally alongside the elongated motor assembly. A flow controller is mounted in the handpiece outer housing. The flow controller comprises an adjustable flow control valve. The adjustable flow control valve intersects with the internal fluid passage of the handpiece outer housing. The motor output shaft of the elongated motor assembly is mechanically connected to a handpiece drive shaft. The handpiece drive shaft is rotatable about a handpiece drive shaft axis. The handpiece drive shaft axis is offset from the motor output shaft axis. The handpiece drive shaft comprises a drive shaft fluid passage. The drive shaft fluid passage is in fluid communication with the internal fluid passage of the handpiece outer housing.

BRIEF DESCRIPTION OF THE DRAWINGS

These and other features, aspects and advantages of the present invention will now be described with reference to the drawings of a preferred embodiment. The embodiment is intended to illustrate certain features, aspects and advantages of the present invention. The embodiment is not intended to limit the invention.

DETAILED DESCRIPTION OF THE PREFERRED EMBODIMENT

Figure 1:
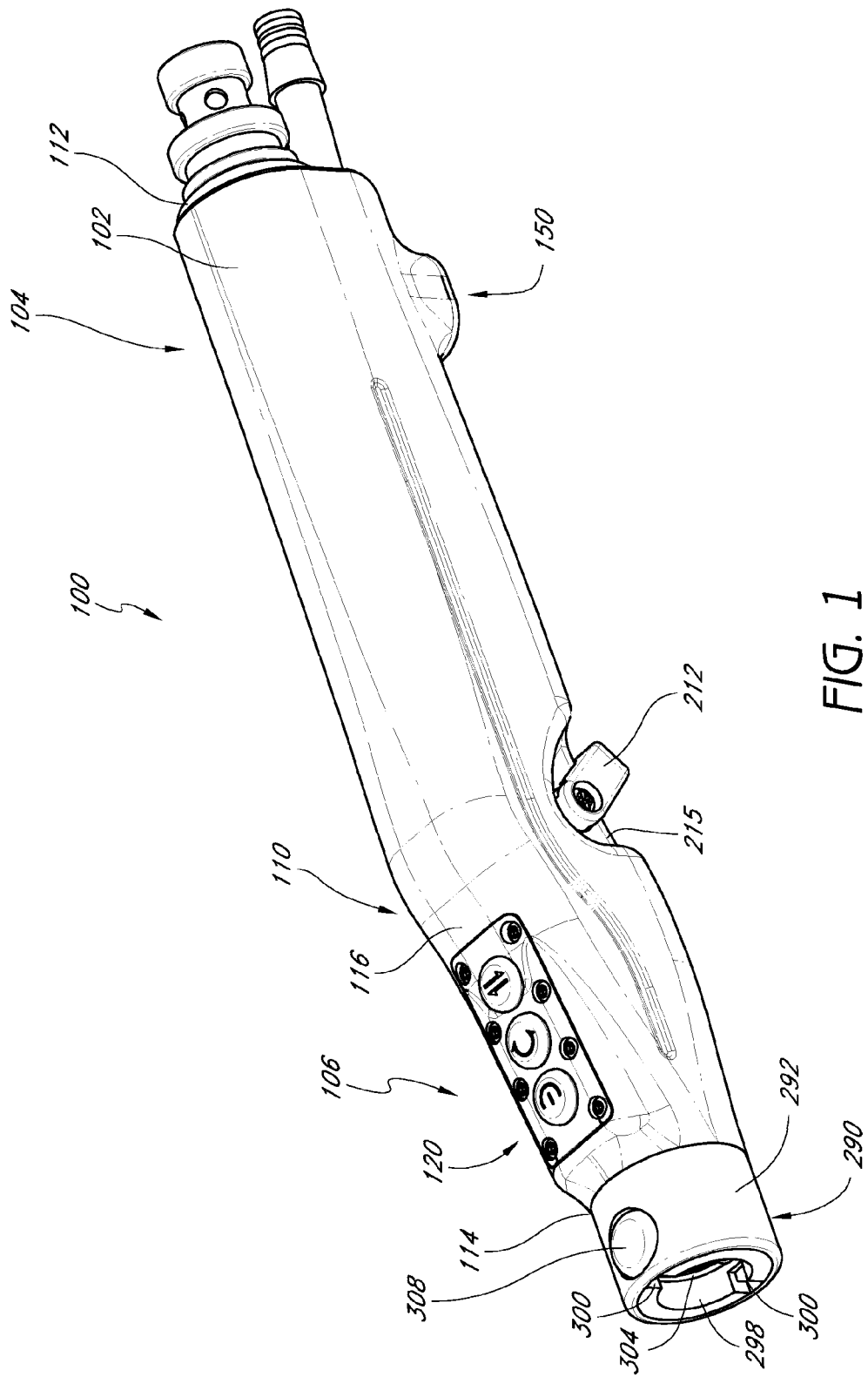
FIG. 1 is a perspective view of an embodiment of a handpiece that is arranged and configured in accordance with certain features, aspects and advantages of the present invention.

FIG. 1 shows a perspective view of an embodiment of a handpiece 100 that is arranged and configured in accordance with certain features, aspects and advantages of the present invention. The illustrated handpiece can be an arthroscopic shaver or can be any other type of handheld medical device that would benefit from any or all of the later described features, aspects and advantages of the present invention.

With continued reference initially to FIG. 1, the illustrated handpiece 100 comprises an outer housing 102. The outer housing 102 can be formed of any suitable material and in any suitable manner. The outer housing 102 preferably is impervious to liquids. More preferably, the outer housing is capable of being autoclaved or sterilized in some other manner. In some embodiments, the outer housing 102 is a single piece component while, in other embodiments, the outer housing 102 is formed by multiple components that are joined together in any suitable manner.

As illustrated, some embodiments have a proximal portion 104 and a distal portion 106 that are connected by an offset portion 110. The offset portion 110 results in the handpiece 100 have a slight offset between a proximal end 112 and a distal end 114. The offset construction offers certain desirable ergonomic advantages. Moreover, the offset construction enables a gear train (described below) to be used such that ratio changes can be possible. In the illustrated embodiment, the proximal portion 104 is offset above the distal portion 106 such that a downwardly sloping surface 116 can be defined along a top side of the handpiece 100.

Figure 2:
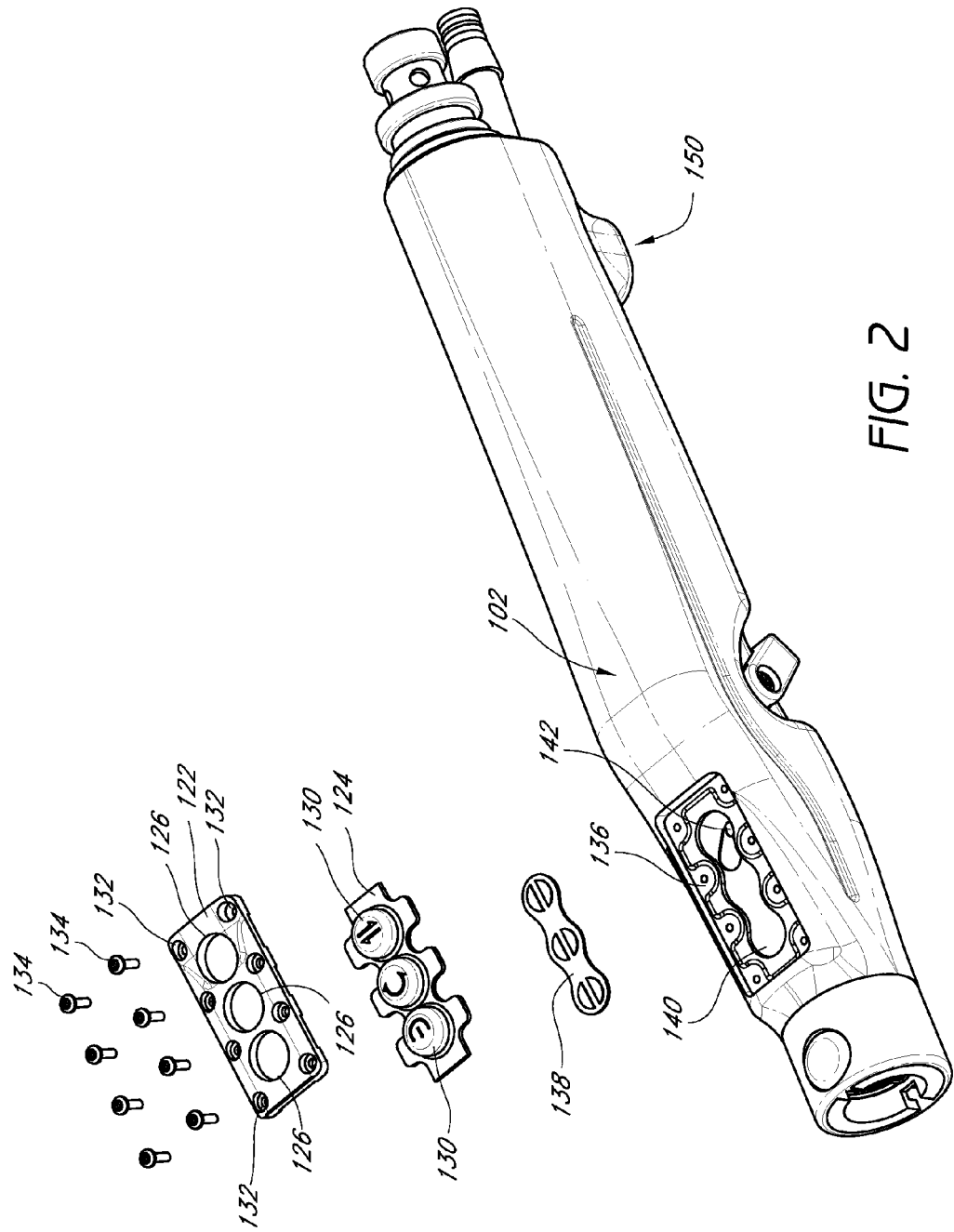
FIG. 2 is an exploded perspective view of the embodiment of FIG. 1.

With continued reference to FIG. 1, the sloping surface 116 preferably contains a first button assembly 120. FIG. 2 shows an exploded view of the handpiece 100. The first button assembly 120 preferably comprises a cover plate 122 and a boot 124. The cover plate 122 can comprise openings 126 while the boot 124 comprises nubs 130 that extend into the opening 126. In some embodiments, the nubs 130 extend upward beyond an upper surface of the cover plate 122.

The cover plate 122 also comprises holes 132, which are countersunk in the illustrated configuration. The holes 132 receive threaded fasteners 134. The fasteners 134 secure the cover plate within or over a recess 136 defined within the outer housing 102. The recess 136 preferably is shaped and configured to receive the boot 124 with the cover plate 122 tightly securing the boot 124 in position. Thus, the combination of the recess 136, the boot 124 and the cover plate 122 advantageously can define a liquid tight assembly. Such a liquid tight assembly can protect internal connections and components during use and during cleaning, for instance.

Underlying the boot 124, a printed circuit board 138 is positioned in a further recess 140. The printed circuit board 138 preferably is spaced apart from the boot 124. More preferably, the boot 124 comprises a metallic component, such as a gold component for example, that underlies each nub 130 and the printed circuit board 138 comprises a corresponding metallic component that can be contacted by the metallic component of the boot 124. Thus, when the nub 130 is depressed, the nub 130 and the metallic component come into contact with the metallic component of the printed circuit board 138 to close the circuit when the nub 130 has been depressed. In other words, the first button assembly preferably is a contact button assembly. Other configurations are possible.

In some embodiments, a single passage 142 extends through a portion of the outer housing 102 between control circuitry for the handpiece and the first button assembly 120. The passage 142 connects the push button circuitry to inner portions of the handpiece 102.

With reference now to FIG. 1, the handpiece 100 also comprises a second button assembly 150. As shown in FIG. 1, the first button assembly 120 and the second button assembly 150 are positioned on opposite axial ends of the handpiece 100. In the illustrated construction, the first button assembly 120 is on at least one of the distal portion 106 and the offset portion 110 while the second button assembly 150 is on the proximal portion 104 of the handpiece 100. In addition, in the illustrated construction, the first button assembly 120 is positioned on a top portion of the handpiece 100 while the second button assembly 150 is on a bottom portion of the handpiece 100. Thus, in some embodiments, the first button assembly 120 and the second button assembly 150 are on diametrically opposite portions of the handpiece 100. The illustrated configuration advantageously multiplies the available hand-holding positions as a result of the dual button assemblies and the locations of the dual buttons.

Figure 3:
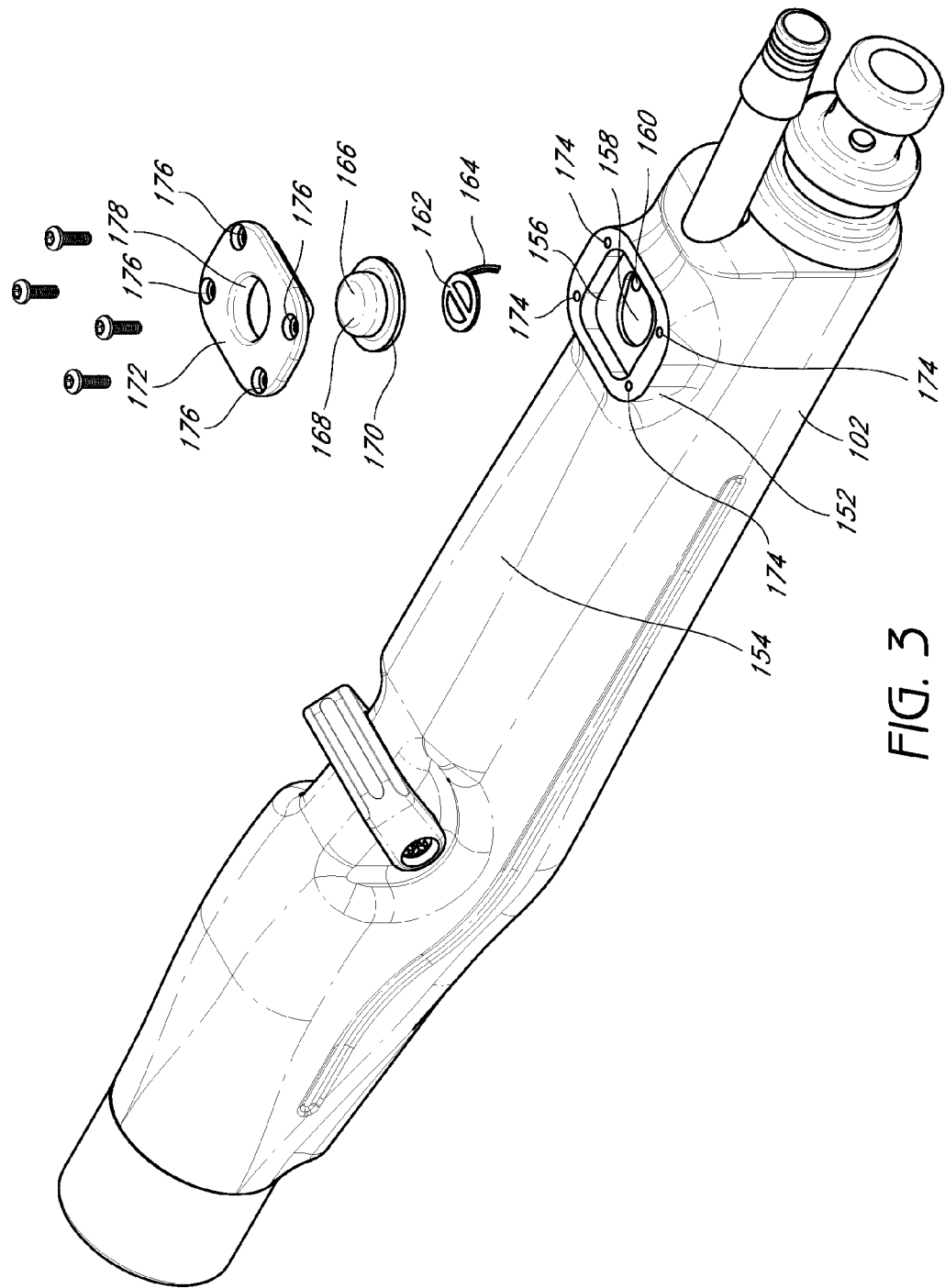
FIG. 3 is another exploded perspective view of the embodiment of FIG. 1.

With reference now to FIG. 3, the second button assembly 150 preferably is mounted to a boss 152. The boss 152 extends outward from a lower surface 154 in FIG. 1 as shown in FIG. 2. In the illustrated configuration, the boss 152 defines a first recess 156, within which a second recess 158 is defined.

A passage 160 extends from the second recess 158 into an internal portion of the handpiece 100.

A printed circuit board 162 is sized and configured for placement within the second recess 158. Wires 164 extend from the printed circuit board 162 and extend into and through the passage 160. A boot 166 fits within the first recess 156 and substantially covers the second recess 158. The boot 166 comprises a nub 168 and a flange 170. In some configurations, the flange 170 rests upon a surface defined within the first recess 156 while the nub 168 overlies a metallic component on the printed circuit board 162. Preferably, the nub 168 and the printed circuit board 162 are spaced apart. The second button assembly 150 preferably defines a contact switch but other configurations are possible.

A cover plate 172 overlies at least a portion of the illustrated boss 152. In the illustrated configuration, the boss 152 comprises a plurality of threaded holes 174 and the cover plate 172 comprises corresponding holes 176. The holes 176 in the cover plate 172 preferably are countersunk and receive threaded fasteners which secure the cover plate 172 in position over the boss 152. Preferably, the cover plate 172 has a portion that is received within the first recess 156 such that the cover plate 172 compresses the flange 170 of the boot 166 against the surface in the first recess 156. In this manner, the second button assembly 150 comprises a substantially liquid tight construction.

With continued reference to FIG. 3, the cover plate 172 also comprises a central opening 178. The nub 168 of the boot 166 can extend into, and in some embodiments, through, the central opening 178. Similar to the first button assembly 120, the printed circuit board 162 preferably is spaced apart from the boot 166. More preferably, the boot 166 comprises a metallic component on a lower surface of the nub 168 and the printed circuit board 162 comprises a corresponding metallic component. The metallic component of the nub 168 can close a circuit when it comes into contact with the metallic component of the printed circuit board 162. In other words, the second button assembly 150 also preferably is a contact button assembly.

The first and second button assemblies 120, 150 can be electrically connected to a controller that controls the functions of the handpiece 100. In one preferred configuration, the first button assembly 120 can comprise a plurality of control members or buttons such that, for instance, the button assembly 120 has an on/off or power control, a direction control button and a speed control button (e.g., up speed and/or down speed) while the second button assembly 150 can comprise at least one additional power button. Thus, the two button assemblies 120, 150, in some configurations, can provide duplicative power buttons. Other configurations are possible. For example, at least one button of the first button assembly 120 and at least one button of the second button assembly 150 can have a single function such that the two buttons control a single function (e.g., power or reversing motion or speed or the like).

Figure 4:
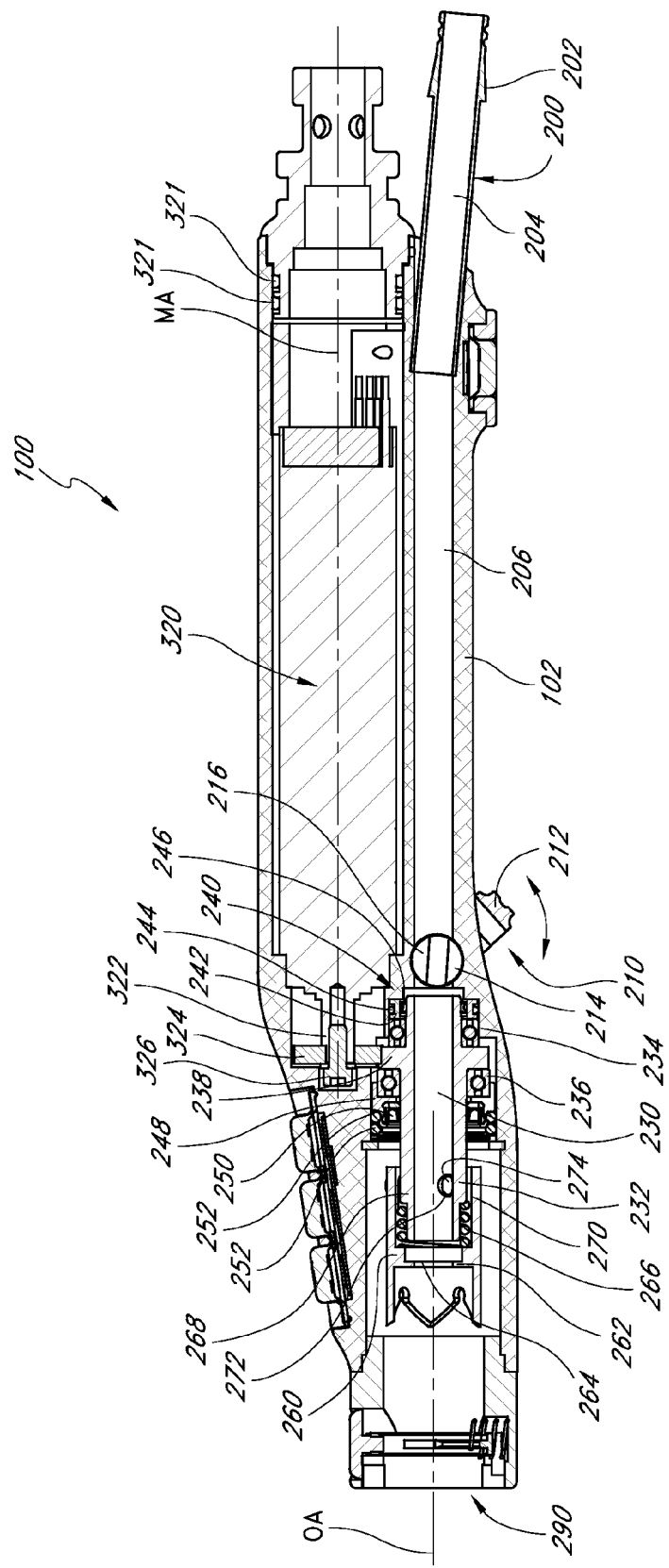
FIG. 4 is a sectioned view of the embodiment of FIG. 1.
Figure 5:
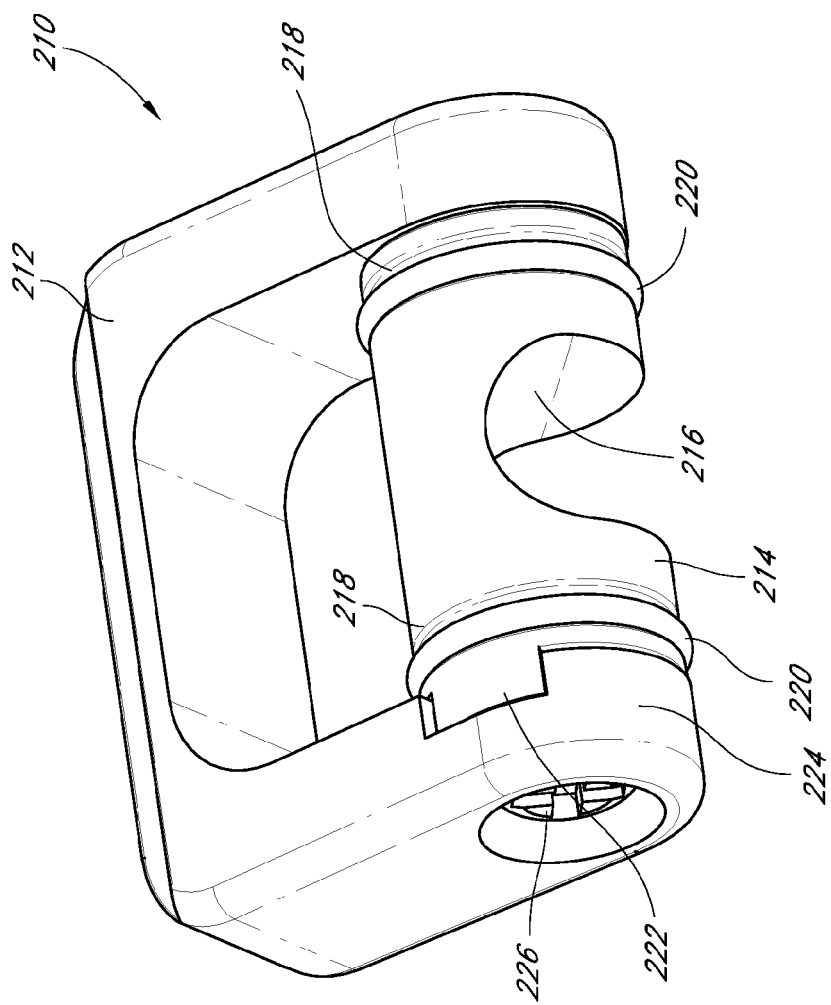
FIG. 5 is an enlarged perspective view of a flow controller used with the embodiment of FIG. 1.

With reference now to FIG. 4, the illustrated handpiece 100 is designed for use with cannulated cutting instruments, for instance. Thus, a fluid inlet 200 is shown extending from a rear of the illustrated handpiece 100. The fluid inlet 200 can comprise a barbed or other suitable coupling configuration 202 at a proximal end. The coupling configuration 202 is used to join the fluid inlet 200 to a suitable fluid source.

The fluid inlet 200 also defines a fluid passage 204. The fluid passage 204 is fluidly connected to a handpiece fluid passage 206. Preferably, the handpiece fluid passage 206 is an integrated passage that is internal to the outer housing 102. In some configurations, the handpiece fluid passage 206 can be an external hose; however, the integrated design of the illustrated configuration is desired due to the improved cleaning and maintenance characteristics of such an integrated construction.

Flow through the fluid passage 206 can be controlled in any suitable manner. A flow controller 210 can be positioned along a suitable portion of the handpiece fluid passage 206 or another fluidly connected portion of the fluid passage either internal to the handpiece or external to the handpiece 100. With reference to FIG. 4, the illustrated flow controller 210 comprises a handle 212 that is joined for rotation with a flow control cylinder 214. The handle 212 preferably is positioned within lateral recesses 215 defined within the outer housing 102 of the handpiece. Moreover, at least a portion of the handle 212 preferably extends downward below a surface of the handpiece to allow easy manipulation of the handle 212. Other configurations are possible.

The cylinder comprises an inner wall 216 that defines a flow passage that partially corresponds to the handpiece flow passage 206. To each side axially of the flow passage, the cylinder 214 comprises a groove 218 that receives a sealing member, such as an o-ring 220. The o-rings 220 interface between the cylinder 214 and an inner surface of the handpiece. As such, the o-rings 220 help reduce the likelihood of a fluid leak from the fluid passage 206 or the flow controller 210.

The illustrated cylinder 214 comprises a split stepped surface 222 at one axial end. The split stepped surface 222 of the cylinder 214 mates with a split stepped surface 224 of the handle 212. By providing the mating surfaces, the handle 212 and the cylinder 214 can be positively coupled together for rotation. Other configurations are possible. The handle 212 and the cylinder 214 can be joined together by a threaded fastener 226 at each end. Other configurations also are possible.

When the cylinder 214 is positioned in the handpiece fluid passage 206, the handle 212 can have a passage-open position and a passage-closed position depending upon the angular orientation of the handle 212 (and therefore the passage through the cylinder 214 defined by the wall 216) relative to the handpiece 100. In the illustrated configuration, the passage is opened when the handle 212 is oriented toward the proximal end of the handpiece 100 while the passage is closed as the handle is rotated in the clockwise direction in FIG. 4.

With continued reference to FIG. 4, the handpiece fluid passage 206 couples with a fluid passage 230 defined within a drive shaft 232. The drive shaft 232 is journaled for rotation (which includes oscillation) by a first bearing 234 and a second bearing 236. In the illustrated configuration, a gear 238 is integrally formed with, or separately formed and secured to, the drive shaft 232. The gear 238 preferably is interposed between the first bearing 234 and the second bearing 236.

With continued reference to FIG. 4, a seal assembly 240 preferably is positioned adjacent to the first bearing 234. The seal assembly can comprise a ring member 242 with a first seal 244 positioned to an outside of the ring member 242 and a second seal 246 positioned inside of the ring member 242. The first seal 244, which can be an o-ring, is interposed between the ring member 242 and a recess formed within the outer housing 102. The second seal 246, which can be a quad o-ring, is interposed between the ring member 242 and the shaft.

A bushing 248 can overlie an outer portion of the second bearing 236. A seal 250, such as a lip seal or the like, can be positioned between at least a portion of the bushing 248 and the shaft 232 while two or more seals 252, such as o-rings, can be positioned between a portion of the bushing 248 and a surface of the outer housing 102 that defines the recess in which the shaft 232 extends. A seal washer 254 and a spring washer 256 enclose the seal assembly within the recess of the outer house 102. Other configurations also are possible.

The drive shaft 232 extends into a drive hub 260. At least a portion of the drive hub 260 preferably surrounds at least a portion of the drive shaft 232. The illustrated drive hub 260 comprises a centrally positioned flange 262. The flange 262 defines a central passage 264 that is in fluid communication with the passage 230 that extends through the drive shaft 232. In addition, as will be described below, the flange 262 defines a tool seat against which a tool used with the handpiece 100 can bear. Furthermore, the flange 262 supports a spring 266.

With continued reference to FIG. 4, the spring 266 extends between the flange 262 of the drive hub 260 and a step 268 formed on a surface of the drive shaft 232. In some embodiments, the step 268 is formed on an outer surface of the drive shaft 232. The spring 266 biases apart the drive hub 260 and the drive shaft 232.

The drive hub 260 preferably comprises a slot 270 that is formed in a portion of the drive hub 260 that overlaps with the drive shaft 232. The drive shaft 232 comprises an opening 272 that generally corresponds with the slot 270 through the drive hub 260. In some embodiments, the drive shaft can comprise a slot while the drive hub comprises an opening. Other configurations also are possible. A pin 274 is inserted on each side of the opening 272 and the slot 270 such that the drive hub 260 and the drive shaft 232 are generally coupled for rotation (which includes oscillation) while allowing some degree of axial movement for reasons that will be discussed below. In some embodiments, at least two such pin, slot and opening assemblies can be positioned around the periphery for coupling to allow for fluid flow through the cannulated shaft. In any event, such assemblies preferably are symmetrically spaced about the periphery for balance of the handpiece 100 during rotation (which includes oscillation).

Figure 6:
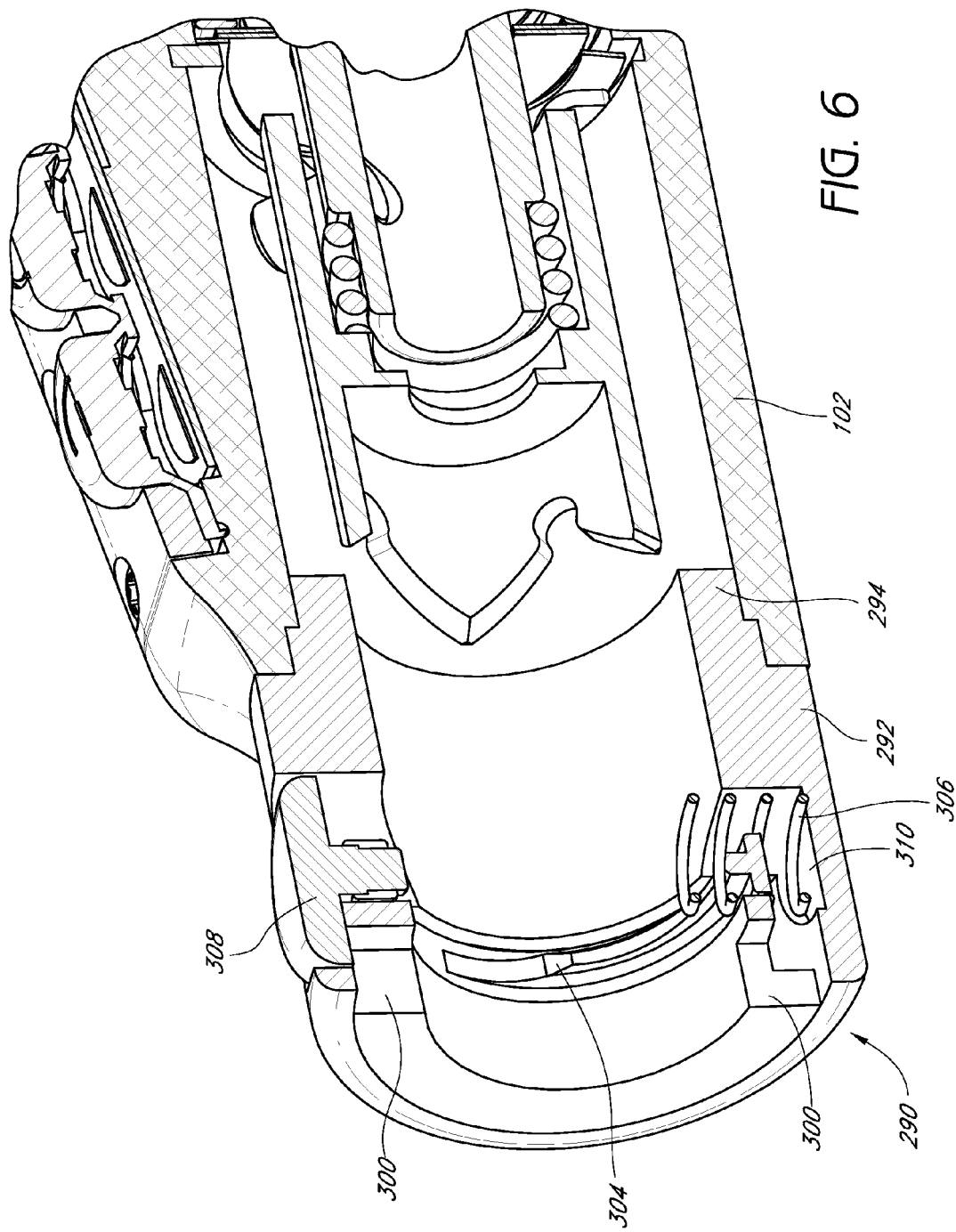
FIG. 6 is an enlarged partially sectioned perspective view of a collet mechanism used in the embodiment of FIG. 1.
Figure 7:
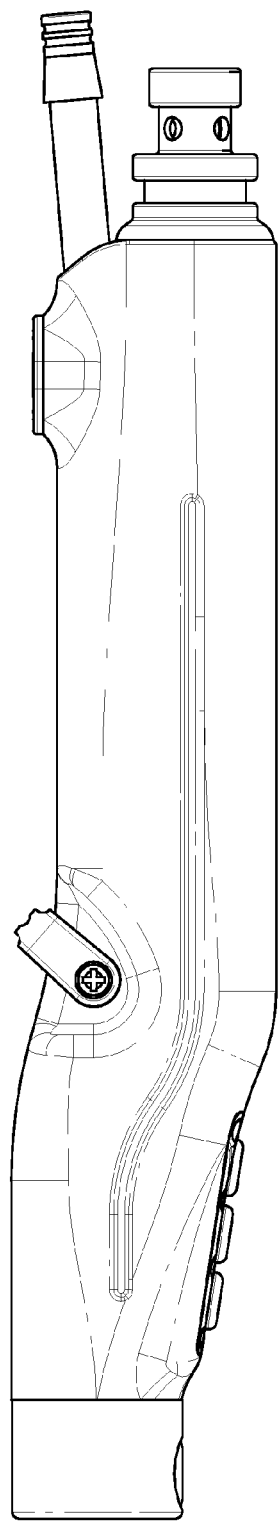
FIG. 7 is a side view of the embodiment of FIG. 1 with the other side view being a mirror image of FIG. 7.
Figure 9:
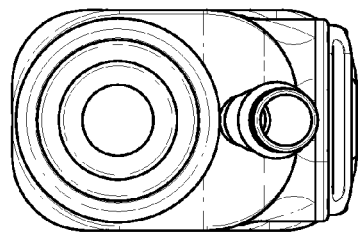
FIG. 9 is another end view of the embodiment of FIG. 1.
Figure 8:
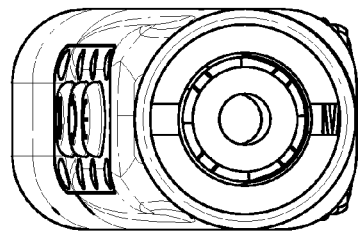
FIG. 8 is an end view of the embodiment of FIG. 1.
Figure 10:
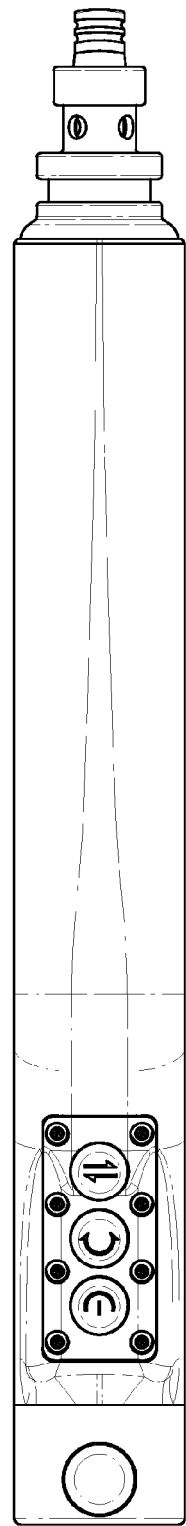
FIG. 10 is a top view of the embodiment of FIG. 1.
Figure 11:
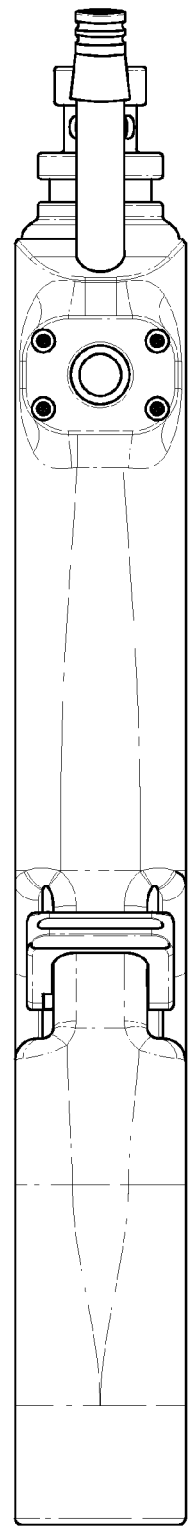
FIG. 11 is a bottom view of the embodiment of FIG. 1.

With reference now to FIG. 6, a collet mechanism 290 is shown in a partial view of the embodiment of FIG. 1. As illustrated, the collet mechanism 290 comprises a housing extension 292. The housing extension 292 can be connected to the outer housing in any suitable manner. The illustrated extension 292 comprises a proximal end 294 with a stepped configuration. The stepped configuration is received within the distal end of the outer housing 102.

A closure ring 298 preferably is pressed into a distal end 296 of the extension 292. The closure ring 298 can comprise a press-fit outer surface that presses into an inner surface of the extension. A pair of slots 300 can be aligned with the collet button 308 to help orient a cutting attachment, for example, when coupling the cutting attachment to the handpiece.

A generally cylindrical insert 302 can be mounted between the closure ring 298 and a stepped inner surface 304 of the extension 292. The cylindrical insert 302 preferably is loosely retained in position. More preferably, the cylindrical insert 302 is capable of radial movement relative to the extension 292.

As illustrated, the cylindrical insert 302 comprises a rib 304 that extends about half way around an inner circumference of the insert 302. The rib 304 is sized, shaped and configured to engage a groove formed on a cutting tool attachment, such as a groove in a shaft of a blade attachment. Other configurations are possible. In addition, in some configurations, a distal surface of the rib 304 can slope such that insertion of a tool shaft into the distal end of the extension 292 causes the sloped surface to move the insert 302 radially in the direction of the rib 304.

With continued reference to FIG. 6, the insert 302 is biased by a spring 306 upwardly in FIG. 6. To move the insert 302 downward against the biasing force of the spring 306, a button 308 can be secured to, or in contact with, the insert 302. FIG. 6 illustrates the insert 302 in a lowermost position, such as would be expected upon depression of the button 308. The spring 306 can be received within a recess 310 formed in the extension 292. Other configurations also are possible.

In use, a shaft of a blade attachment is inserted into the collet mechanism 290. As the shaft is inserted, the end of the shaft bears against the flange 262 of the drive hub 260. When the shaft continues to be inserted, the drive hub 260 is moved against the bias of the spring 266 until the rib 304 of the insert 302 in the collet mechanism 290 locks into a groove formed on the shaft of the blade attachment. Once the rib 304 locks into the groove, the blade attachment is engaged in the drive hub 260. The drive hub has end features that engage with corresponding features of the blade attachment such that rotation (including oscillation) of the drive hub results in rotation (including oscillation) of the blade attachment.

To release the blade attachment from the handpiece 100, the button 308 of the collet mechanism 290 is depressed to release the blade attachment. Depressing the button 308 forces the insert 302 downward relative to the housing extension 292 against the biasing force of the spring 306. Downward movement of the insert 302 allows the rib 304 to disengage from a groove of the blade attachment, which allows the blade attachment to be removed from the handpiece. Once the rib 304 disengages, the spring 266 urges the drive hub 260 forward such that the blade attachment moves forward and the rib 304 no longer is axially aligned with the groove of the blade attachment. Other suitable constructions also are possible.

With reference again to FIG. 4, a motor assembly 320 can be mounted in the outer housing 102. Any suitable motor assembly can be used and the motor can be air driven, fluid driven or electric, for example. Preferably, seals 321 are provided that generally seal the motor assembly 320 within the outer housing 102. Thus, in combination with the sealing components described above, the outer housing 102 generally is impervious or substantially impervious to fluids.

In the illustrated configuration, the motor assembly 320 comprises an output shaft 322. The output shaft 322 rotates (which includes oscillation) about a motor axis MA. The motor axis MA is offset from an output axis OA. In other words, the motor axis MA is not axially aligned with the output axis OA.

The output shaft 322 carries a drive gear 324. In some configurations, a fastener 326 secures the drive gear 324 to an end of the output shaft 322. The drive gear 324 meshes with the gear 238 that is mounted to, or integrally formed with, the drive shaft 232. Preferably, the drive gear 324 and the gear 238 are configured to reduce the rotational speed from the motor assembly 320 to the drive hub 260. Other configurations also are possible.

Although the present invention has been disclosed in the context of certain preferred embodiments, examples and variations, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is specifically contemplated that various combinations or subcombinations of the specific features and aspects of the embodiments may be made and still fall within the scope of the invention. It should be understood that various features and aspects of the disclosed embodiments can be combined with or substituted for one another in order to form varying modes of the disclosed invention. Moreover, some variations that have been described with respect to one embodiment and not another embodiment can be used with such other embodiments. For instance, many of the embodiments feature reinforcing members. It is intended that the embodiments not featuring reinforcing members can use reinforcing members. Many other variations also have been described herein and cross-application is intended where physically possible. Moreover, it is anticipated that different assemblies can be used on the same eyewear or all assemblies can have a single construction. Thus, it is intended that the scope of the present invention herein disclosed should not be limited by the particular disclosed embodiments described above, but should be determined only by a fair reading of the claims that follow.

What is claimed is:

1. A medical handpiece comprising a handpiece outer housing, the handpiece outer housing enclosing an elongated motor assembly, the elongated motor assembly comprising a motor output shaft, the motor output shaft rotating about a motor output shaft axis, the handpiece outer housing also enclosing an internal fluid passage, the internal fluid passage extending generally parallel to the motor output shaft axis, the internal fluid passage also extending generally alongside the elongated motor assembly, a flow controller being mounted in the handpiece outer housing, the flow controller comprising an adjustable flow control valve, the adjustable flow control valve intersecting with the internal fluid passage of the handpiece outer housing, the motor output shaft of the elongated motor assembly being mechanically connected to a handpiece drive shaft, the handpiece drive shaft being rotatable about a handpiece drive shaft axis, the handpiece drive shaft axis being offset from the motor output shaft axis, the handpiece drive shaft comprising a drive shaft fluid passage, the drive shaft fluid passage being in fluid communication with the internal fluid passage of the handpiece outer housing, the handpiece further comprising a drive hub that is connected to the handpiece shaft, and a spring mounted between a portion of the drive hub and a portion of the handpiece drive shaft such that the drive hub is biased in a distal axial direction relative to the handpiece drive shaft.

2. The medical handpiece of claim 1, wherein the handpiece drive shaft axis extends along a length of the drive shaft fluid passage wherein the handpiece drive shaft axis extends along the internal fluid passage of the handpiece outer housing.

3. The medical handpiece of claim 1 further comprising a first button assembly and a second button assembly, the first button assembly being position on a distal portion of the handpiece outer housing and the second button assembly being positioned on a proximal portion of the handpiece outer housing.

4. The medical handpiece of claim 3, wherein the first button assembly is on an upper portion of the handpiece outer housing and the second button assembly is on a lower portion of the handpiece outer housing.

5. The medical handpiece of claim 3, wherein the first button assembly and the second button assembly each comprises a button having a first functionality such that the button of the first button assembly and the button of the second button assembly have control a single function of the handpiece.

6. The medical handpiece of claim 3, wherein the first button assembly and the second button assembly each comprise a contact button construction.

7. The medical handpiece of claim 1, wherein the handpiece outer housing comprises a distal end, a housing extension connected to the distal end of the handpiece outer housing, a collet mechanism positioned within the housing extension.

8. The medical handpiece of claim 7, wherein the collet mechanism comprises a radially movable component, the radially movable component being biased into a locked portion and being movable to an unlocked position by depressing a button that contacts a portion of the radially movable component.

9. The medical handpiece of claim 8, wherein the radially movable component comprises a ring having an inner circumferential surface, the ring comprising a rib that extends inward from only a portion of the inner circumferential surface of the ring.

10. The medical handpiece of claim 9, wherein the rib is position on a first portion of the ring and the button contacts an opposite portion of the ring.

11. The medical handpiece of claim 1, wherein one of the drive hub and the handpiece drive shaft comprises a hole and the other comprises a slot with a pin extending through both the hole and the slot such that the drive hub is axially movable over a limited range relative to the handpiece drive shaft.

12. The medical handpiece of claim 1, wherein the motor output shaft carries a motor gear that meshes with a handpiece drive shaft gear, the handpiece drive shaft being supported by a first bearing and a second bearing with the handpiece drive shaft gear being interposed between the first bearing and the second bearing.

13. The medical handpiece of claim 12, wherein a proximal seal assembly is positioned proximally of the first bearing and a distal seal assembly is positioned distally of the second bearing.

14. The medical handpiece of claim 1, wherein the drive hub and the drive shaft are coupled for rotation.

15. The medical handpiece of claim 1, further comprising at least one seal having a radial center that is positioned generally co-axial with the motor output shaft axis, the seal extending radially outward of at least some of the elongated motor assembly.

16. The medical handpiece of claim 1, wherein the seal extends radially inward from an inside surface of the outer housing.

17. The medical handpiece of claim 1, further comprising at least one seal configured to inhibit liquids from reaching the elongated motor assembly.

18. The medical handpiece of claim 17, wherein the at least one seal is located near a longitudinal end of the elongated motor assembly.

19. The medical handpiece of claim 1, further comprising at least one seal configured to generally seal an end of the elongated motor assembly that is longitudinally opposite another end of the elongated motor assembly from which the motor output shaft extends.

* * * * *